United States Patent [19]

Romano et al.

[11] Patent Number: 6,048,836
[45] Date of Patent: Apr. 11, 2000

[54] USE OF A COMBINATION OF SURFACTANTS, CHELATING AGENTS AND ESSENTIAL OILS FOR EFFECTIVE DISINFECTION

[75] Inventors: Nicoletta Romano; Marina Trani, both of Rome, Italy; Keith Homer Baker, Union Township, Ohio

[73] Assignee: The Procter & Gamble Company, Cincinnati, Ohio

[21] Appl. No.: 09/214,937

[22] PCT Filed: Jul. 16, 1996

[86] PCT No.: PCT/US96/11763

§ 371 Date: Jan. 15, 1999

§ 102(e) Date: Jan. 15, 1999

[87] PCT Pub. No.: WO98/02044

PCT Pub. Date: Jan. 22, 1998

[51] Int. Cl.[7] ............................. C11D 1/90; C11D 7/18; C11D 3/30; C11D 3/50
[52] U.S. Cl. ................ 510/490; 510/101; 510/130; 510/138; 510/123; 510/199; 510/202; 510/237; 510/251; 510/309; 510/310; 510/362; 510/363; 510/365; 510/367; 510/372; 510/463; 510/477; 510/480; 510/490; 510/424
[58] Field of Search ........................ 510/130, 138, 510/155, 101, 104, 106, 199, 202, 237, 251, 362, 363, 365, 427, 428, 432, 463, 477, 480, 490, 503, 302, 123, 309, 310, 361, 372, 424

[56] References Cited

U.S. PATENT DOCUMENTS

| | | | |
|---|---|---|---|
| 4,589,994 | 5/1986 | Moseman | 252/107 |
| 4,963,287 | 10/1990 | Hutchings et al. | 252/187.23 |
| 5,174,990 | 12/1992 | Douglas | 424/53 |
| 5,403,587 | 4/1995 | McCue et al. | 424/195.1 |
| 5,540,853 | 7/1996 | Trinh et al. | 510/101 |
| 5,562,850 | 10/1996 | Woo et al. | 510/151 |
| 5,607,980 | 3/1997 | McAtee et al. | 514/476 |
| 5,972,322 | 10/1999 | Rath et al. | 424/70.11 |

FOREIGN PATENT DOCUMENTS

| | | |
|---|---|---|
| 288689 | 11/1988 | European Pat. Off. . |
| 467618 | 1/1992 | European Pat. Off. . |
| 1237874 | 6/1971 | United Kingdom . |

*Primary Examiner*—Mark Kopec
*Assistant Examiner*—Charles Boyer
*Attorney, Agent, or Firm*—I. S. Robinson; K. W. Zerby; J. C. Rasser

[57] ABSTRACT

The present invention relates to the use, in a composition, of a combination of a chelating agent, a surfactant, and an essential oil or an active thereof, to provide disinfecting properties to said composition.

15 Claims, No Drawings

USE OF A COMBINATION OF SURFACTANTS, CHELATING AGENTS AND ESSENTIAL OILS FOR EFFECTIVE DISINFECTION

This application is filed pursuant to 35 USC 371 based upon PCT/US96/11763 filed Jul. 16, 1996.

TECHNICAL FIELD

The present invention relates to antimicrobial compositions which can be used to disinfect and clean various surfaces including hard surfaces or in laundry applications.

BACKGROUND

Antimicrobial compositions include materials which have the ability to disinfect. It is generally recognised that a disinfecting material greatly reduces or even eliminates the microorganisms existing on a surface. Antimicrobial compositions have been described in the art which include strong disinfecting materials which are not fully satisfactory from an environmental and/or human safety point of view. For example, typical disinfecting materials used in antimicrobial compositions include quaternary ammonium.

Also, a drawback associated with antimicrobial compositions based on strong disinfecting materials like peracids and/or halogen-releasing compounds, e.g., hypochlorite, is that they may damage surfaces onto which they are contacted to perform their disinfecting action. Indeed, such antimicrobial compositions based on peracids and/or hypochlorite are perceived by the consumers as being not safe to various surfaces including hard-surfaces and fabrics, especially delicate fabrics like silk, wool and the like.

It is therefore an object of the present invention to provide effective disinfection using ingredients which are perceived to have a limited detrimental impact on surfaces and/or to be environmental friendly.

This object can be met by combining in a composition a surfactant, a chelating agent and an antimicrobial essential oil, or an active thereof. Indeed, it has been found that the incorporation, in a composition, of the combination of a surfactant, a chelating agent and an antimicrobial essential oil, or an active thereof, provides disinfecting properties to said composition. Actually, a composition comprising said combination provides excellent disinfection on a surface, even at high dilution levels, i.e., up to dilution levels of from 1:100 (composition:water).

By combining a chelating agent, a surfactant and an essential oil or an active thereof, disinfection may be provided on all types of surfaces including hard-surfaces as well as in laundry applications, or even in human application.

An advantage of the present invention is that excellent disinfection is provided on a broad range of bacterial pure strains including Gram positive and Gram negative bacterial strains and more resistant micro-organisms like fungi.

Another advantage of the present invention is that beside the disinfection properties delivered, good cleaning is also provided.

Representative of the prior art is for example EP-B-288 689 which discloses a liquid for hard-surfaces comprising antimicrobial effective amounts of pine oil and at least one oil soluble organic acid.

U.S. Pat. No. 5,403,587 discloses aqueous antimicrobial compositions which can be used to sanitise, disinfect, and clean hard-surfaces. More particularly, U.S. Pat. No. 5,403, 587 discloses aqueous compositions (pH 1 to 12) comprising essential oils (0.02% to 5%), which exhibit antimicrobial properties efficacy such as thyme oil, eucalyptus oil, clove oil and the like, and a solubilizing or dispersing agent sufficient to form an aqueous solution or dispersion of said essential oils in a water carrier.

Co-pending European patent application number 96870017.9 discloses disinfecting compositions comprising hydrogen peroxide, an antimicrobial essential oil, optionally surfactants and chelating agents.

None of these prior art documents discloses that by combining a chelating agent, a surfactant and an antimicrobial essential oil or an active thereof excellent disinfecting properties are delivered to a surface, even under diluted conditions.

SUMMARY OF THE INVENTION

The present invention encompasses the use, in a composition, of a combination of a chelating agent, a surfactant and an antimicrobial essential oil or an active thereof, to provide disinfecting properties to said composition.

DETAILED DESCRIPTION OF THE INVENTION

A first essential ingredient of the present invention is a chelating agent, or a mixture thereof. Suitable chelating agents to be used herein may be any chelating agent known to those skilled in the art such as the ones selected from the group comprising phosphonate chelating agents, amino carboxylate chelating agents or other carboxylate chelating agents, or polyfunctionally-substituted aromatic chelating agents or mixtures thereof. It has now been found that a chelating agent in combination with a surfactant when added on top of an antimicrobial essential oil and/or an active thereof, in a composition, improves the disinfecting properties of said composition.

Such phosphonate chelating agents may include etidronic acid (1-hydroxyethylidene-bisphosphonic acid or HEDP) as well as amino phosphonate compounds, including amino alkylene poly (alkylene phosphonate), alkali metal ethane 1-hydroxy diphosphonates, nitrilo trimethylene phosphonates, ethylene diamine tetra methylene phosphonates, and diethylene triamine penta methylene phosphonates. The phosphonate compounds may be present either in their acid form or as salts of different cations on some or all of their acid functionalities. Preferred phosphonate chelating agents to be used herein are diethylene triamine penta methylene phosphonates. Such phosphonate chelating agents are commercially available from Monsanto under the trade name DEQUEST®.

Polyfunctionally-substituted aromatic chelating agents may also be useful in the compositions herein. See U.S. Pat. No. 3,812,044, issued May 21, 1974, to Connor et al. Preferred compounds of this type in acid form are dihydroxydisulfobenzenes such as 1,2-dihydroxy-3,5-disulfobenzene.

A preferred biodegradable chelating agent for use herein is ethylene diamine N,N'-disuccinic acid, or alkali metal, or alkaline earth, ammonium or substitutes ammonium salts thereof or mixtures thereof. Ethylenediamine N,N'-disuccinic acids, especially the (S,S) isomer have been extensively described in U.S. Pat. No. 4,704,233, Nov. 3, 1987 to Hartman and Perkins. Ethylenediamine N,N'-disuccinic acid is, for instance, commercially available under the tradename ssEDDS® from Palmer Research Laboratories.

Suitable amino carboxylate chelating agents useful herein include ethylene diamine tetra acetate, diethylene triamine pentaacetate, diethylene triamine pentacetate (DTPA), N-hydroxyethylethylenediamine triacetate, nitrilotri-acetate, ethylenediamine tetraproprionate, triethylenetetraaminehexa-acetate, ethanoldiglycine, propylene diamine tetracetic acid (PDTA) and methyl glycine di-acetic acid (MGDA), both in their acid form, or in their alkali metal, ammonium, and substituted ammonium salt forms. Particularly suitable to be used herein are diethylene triamine penta acetic acid (DTPA), propylene diamine tetracetic acid (PDTA) which is, for instance, commercially available from BASF under the trade name Trilon FS® and methyl glycine di-acetic acid (MGDA).

Further carboxylate chelating agents to be used herein include malonic acid, salicylic acid, glycine, aspartic acid, glutamic acid, dipicolinic acid and derivatives thereof, or mixtures thereof.

Typically, the chelating agent, or a mixture thereof, is present in the composition at a level of from 0.001% to 5% by weight, preferably from 0.002% to 3% by weight and more preferably from 0.002% to 1.5%.

A second essential ingredient of the present invention is a surfactant or a mixture thereof.

Suitable surfactants to be used herein may be any surfactant known to those skilled in the art including anionic, nonionic, cationic, amphoteric and/or, zwitterionic surfactants. Said surfactants are desirable as in combination with a chelating agent and an essential oil or an active thereof they provide improved disinfecting performance on the surfaces treated therewith. Also surfactants contribute to the cleaning performance of a composition comprising said combination.

Particularly suitable anionic surfactants to be used herein include water soluble salts or acids of the formula $ROSO_3M$ wherein R is preferably a $C_6$–$C_{24}$ hydrocarbyl, preferably an alkyl or hydroxyalkyl having a $C_{10}$–$C_{20}$ alkyl component, more preferably a $C_{12}$–$C_{18}$ alkyl or hydroxyalkyl, and M is H or a cation, e.g., an alkali metal cation (e.g., sodium, potassium, lithium), or ammonium or substituted ammonium (e.g., methyl-, dimethyl-, and trimethyl ammonium cations and quaternary ammonium cations, such as tetramethyl-ammonium and dimethyl piperdinium cations and quaternary ammonium cations derived from alkylamines such as ethylamine, diethylamine, triethylamine, and mixtures thereof, and the like).

Other suitable anionic surfactants to be used herein include alkyl-diphenyl-ether-sulphonates and alkyl-carboxylates. Other anionic surfactants can include salts (including, for example, sodium, potassium, ammonium, and substituted ammonium salts such as mono-, di- and triethanolamine salts) of soap, $C_9$–$C_{20}$ linear alkylbenzenesulfonates, $C_8$–$C_{22}$ primary or secondary alkanesulfonates, $C_8$–$C_{24}$ olefinsulfonates, sulfonated polycarboxylic acids prepared by sulfonation of the pyrolyzed product of alkaline earth metal citrates, e.g., as described in British patent specification No. 1,082,179, $C_8$–$C_{24}$ alkylpolyglycolethersulfates (containing up to 10 moles of ethylene oxide); alkyl ester sulfonates such as $C_{14-16}$ methyl ester sulfonates; acyl glycerol sulfonates, fatty oleyl glycerol sulfates, alkyl phenol ethylene oxide ether sulfates, paraffin sulfonates, alkyl phosphates, isethionates such as the acyl isethionates, N-acyl taurates, alkyl succinamates and sulfosuccinates, monoesters of sulfosuccinate (especially saturated and unsaturated $C_{12}$–$C_{18}$ monoesters) diesters of sulfosuccinate (especially saturated and unsaturated $C_6$–$C_{14}$ diesters), acyl sarcosinates, sulfates of alkylpolysaccharides such as the sulfates of alkylpolyglucoside (the nonionic nonsulfated compounds being described below), branched primary alkyl sulfates, alkyl polyethoxy carboxylates such as those of the formula $RO(CH_2CH_2O)_kCH_2COO-M^+$ wherein R is a $C_8$–$C_{22}$ alkyl, k is an integer from 0 to 10, and M is a soluble salt-forming cation. Resin acids and hydrogenated resin acids are also suitable, such as rosin, hydrogenated rosin, and resin acids and hydrogenated resin acids present in or derived from tall oil. Further examples are given in "Surface Active Agents and Detergents" (Vol. I and II by Schwartz, Perry and Berch). A variety of such surfactants are also generally disclosed in U.S. Pat. No. 3,929,678, issued Dec. 30, 1975 to Laughlin, et al. at Column 23, line 58 through Column 29, line 23 (herein incorporated by reference).

Preferred anionic surfactants for use in the compositions herein are the alkyl benzene sulfonates, alkyl sulfates, alkyl alkoxylated sulfates, paraffin sulfonates and mixtures thereof.

Suitable amphoteric surfactants to be used herein include betaine and sulphobetaine surfactants, derivatives thereof or mixtures thereof. Said betaine or sulphobetaine surfactants are preferred herein as, they help disinfection by increasing the permeability of the bacterial cell wall, thus allowing other active ingredients to enter the cell.

Furthermore, due to the mild action profile of said betaine or sulphobetaine surfactants, they are particularly suitable for the cleaning of delicate surfaces, e.g. delicate laundry or surfaces in contact with food and/or babies. Betaine and sulphobetaine surfactants are also extremely mild to the skin and/or surfaces to be treated.

Suitable betaine and sulphobetaine surfactants to be used herein are the betaine/sulphobetaine and betaine-like detergents wherein the molecule contains both basic and acidic groups which form an inner salt giving the molecule both cationic and anionic hydrophilic groups over a broad range of pH values. Some common examples of these detergents are described in U.S. Pat. Nos. 2,082,275, 2,702,279 and 2,255,082, incorporated herein by reference. Preferred betaine and sulphobetaine surfactants herein are according to the formula

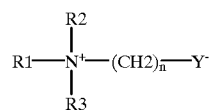

wherein R1 is an alkyl radical containing from 1 to 24 carbon atoms, preferably from 8 to 18, and more preferably from 12 to 14, wherein R2 and R3 contain from 1 to 3 carbon atoms, and preferably 1 carbon atom, wherein n is an integer from 1 to 10, preferably from 1 to 6 and more preferably is 1, Y is selected from the group consisting of carboxyl and sulfonyl radicals and wherein the sum of R1, R2 and R3 radicals is from 14 to 24 carbon atoms, or mixtures thereof.

Examples of particularly suitable betaine surfactants include C12–C18 alkyl dimethyl betaine such as coconutbetaine and C10–C16 alkyl dimethyl betaine such as laurylbetaine. Coconutbetaine is commercially available from Seppic under the trade name of Amonyl 265®. Laurylbetaine is commercially available from Albright & Wilson under the trade name Empigen BB/L®.

Other suitable amphoteric surfactants to be used herein include amine oxides having the following formula $R_1R_2R_3NO$ wherein each of R1, R2 and R3 is independently a saturated substituted or unsubstituted, linear or branched alkyl group of from 1 to 30 carbon atoms, preferably of from 6 to 30 carbon atoms, more preferably of from 10 to 20 carbon atoms, and most preferably of from 8 to 18 carbon atoms. Preferred amine oxides for use herein are for instance natural blend C8–C10 amine oxides as well as C12–C16 amine oxides commercially available from Hoechst. Suitable short chain amine oxides to be used according to the present invention are amine oxides having the following formula $R_1R_2R_3NO$ wherein R1 is a C6 to C10 alkyl group, preferably a C8 to C10 alkyl group and wherein R2 and R3 are independently substituted or unsubstituted, linear or branched alkyl groups of from 1 to 4 carbon atoms, preferably of from 1 to 3 carbon atoms, and more preferably are ethyl groups. R1 may be a saturated linear or branched alkyl group. referred short chain amine oxides for use herein are for instance natural lend C8–C10 amine oxides available from Hoechst.

In a preferred embodiment of the present invention, the surfactant is a surfactant system comprising an amine oxide and a betaine or sulphobetaine surfactant, preferably in a weight ratio of amine oxide to betaine or sulphobetaine of 2:1 to 100:1, more preferably of 6:1 to 100:1. Using such a surfactant system together with a chelating agent and an antimicrobial essential oil or active thereof, in a composition, provides not only effective disinfecting properties and effective cleaning performance to said composition but also provides the cleaned surfaces with a shiny effect, i.e., the amount of filming/streaking left on the cleaned surface that has been treated with said composition is minimal.

Suitable nonionic surfactants to be used herein are fatty alcohol ethoxylates and/or propoxylates which are commercially available with a variety of fatty alcohol chain lengths and a variety of ethoxylation degrees. Indeed, the HLB values of such alkoxylated nonionic surfactants depend essentially on the chain length of the fatty alcohol, the nature of the alkoxylation and the degree of alkoxylation. Surfactant catalogues are available which list a number of surfactants, including nonionics, together with their respective HLB values.

Suitable chemical processes for preparing the nonionic surfactants for use herein include condensation of corresponding alcohols with alkylene oxide, in the desired proportions. Such processes are well known to the man skilled in the art and have been extensively described in the art. As an alternative, a great variety of alkoxylated alcohols suitable for use herein is commercially available from various suppliers.

Particularly suitable to be used herein as nonionic surfactants are hydrophobic nonionic surfactants having an HLB (hydrophilic-lipophilic balance) below 16, preferably below 15, more preferably below 12, and most preferably below 10. Those hydrophobic nonionic surfactants have been found to provide good grease cutting properties.

Preferred hydrophobic nonionic surfactants to be used in the compositions according to the present invention are surfactants having an HLB below 16 and being according to the formula $RO-(C_2H_4O)_n(C_3H_6O)_mH$, wherein R is a $C_6$ to $C_{22}$ alkyl chain or a $C_6$ to $C_{28}$ alkyl benzene chain, and wherein n+m is from 0 to 20 and n is from 0 to 15 and m is from 0 to 20, preferably n+m is from 1 to 15 and, n and m are from 0.5 to 15, more preferably n+m is from 1 to 10 and, n and m are from 0 to 10. The preferred R chains for use herein are the $C_8$ to $C_{22}$ alkyl chains. Accordingly, suitable hydrophobic nonionic surfactants for use herein are Dobanol$^R$ 91-2.5 (HLB=8.1; R is a mixture of C9 and $C_{11}$ alkyl chains, n is 2.5 and m is 0), or Lutensol$^R$ TO3 (HLB=8; R is a $C_{13}$ alkyl chains, n is 3 and m is 0), or Lutensol$^R$ AO3 (HLB=8; R is a mixture of $C_{13}$ and $C_{15}$ alkyl chains, n is 3 and m is 0), or Tergitol$^R$ 25L3 (HLB=7.7; R is in the range of $C_{12}$ to $C_{15}$ alkyl chain length, n is 3 and m is 0), or Dobanol$^R$ 23-3 (HLB=8.1; R is a mixture Of $C_{12}$ and $C_{13}$ alkyl chains, n is 3 and m is 0), or Dobanol$^R$ 23-2 (HLB=6.2; R is a mixture of $C_{12}$ and $C_{13}$ alkyl chains, n is 2 and m is 0), or Dobanol$^R$ 45-7 (HLB=11.6; R is a mixture of $C_{14}$ and $C_{15}$ alkyl chains, n is 7 and m is 0) Dobanol$^R$ 23-6.5 (HLB=11.9; R is a mixture of $C_{12}$ and $C_{13}$ alkyl chains, n is 6.5 and m is 0), or Dobanol$^R$ 25-7 (HLB=12; R is a mixture Of $C_{12}$ and $C_{15}$ alkyl chains, n is 7 and m is 0), or Dobanol$^R$ 91-5 (HLB=11.6; R is a mixture of $C_9$ and $C_{11}$ alkyl chains, n is 5 and m is 0), or Dobanol$^R$ 91-6 (HLB=12.5 ; R is a mixture of $C_9$ and $C_{11}$ alkyl chains, n is 6 and m is 0), or Dobanol$^R$ 91-8 (HLB=13.7; R is a mixture of $C_9$ and $C_{11}$ alkyl chains, n is 8 and m is 0), Dobanol$^R$ 91-10 (HLB=14.2; R is a mixture of $C_9$ to $C_{11}$ alkyl chains, n is 10 and m is 0), or mixtures thereof. Preferred herein are Dobanol$^R$ 91-2.5, or Lutensol$^R$ TO3, or Lutensol$^R$ AO3, or Tergitol$^R$ 25L3, or Dobanol$^R$ 23-3, or Dobanol$^R$ 23-2, or mixtures thereof. These Dobanol$^R$ surfactants are commercially available from SHELL. These Lutensol$^R$ surfactants are commercially available from BASF and these Tergitol$^R$ surfactants are commercially available from UNION CARBIDE.

Suitable zwitterionic surfactants contain both cationic and anionic hydrophilic groups on the same molecule at a relatively wide range of pH's. The typical cationic group is a quaternary ammonium group, although other positively charged groups like phosphonium, imidazolium and sulfonium groups can be used. The typical anionic hydrophilic groups are carboxylates and sulfonates, although other groups like sulfates, phosphonates, and the like can be used. A generic formula for some preferred zwitterionic surfactants is

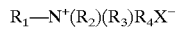

wherein $R_1$ is a hydrophobic group; $R_2$ and $R_3$ are each $C_1$–$C_4$ alkyl, hydroxy alkyl or other substituted alkyl group which can also be joined to form ring structures with the N; $R_4$ is a moiety joining the cationic nitrogen atom to the hydrophilic group and is typically an alkylene, hydroxy alkylene, or polyalkoxy group containing from 1 to 4 carbon atoms; and X is the hydrophilic group which is preferably a carboxylate or sulfonate group. Preferred hydrophobic groups $R_1$ are alkyl groups containing from 8 to 22, preferably less than 18, more preferably less than 16 carbon atoms. The hydrophobic group can contain unsaturation and/or substituents and/or linking groups such as aryl groups, amido groups, ester groups and the like. In general, the simple alkyl groups are preferred for cost and stability reasons.

Other specific zwitterionic surfactants have the generic formulae:

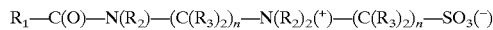

or

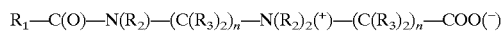

wherein each $R_1$ is a hydrocarbon, e.g. an alkyl group containing from 8 up to 20, preferably up to 18, more preferably up to 16 carbon atoms, each $R_2$ is either a hydrogen (when attached to the amido nitrogen), short chain alkyl or substituted alkyl containing from one to 4 carbon atoms, preferably groups selected from the group consisting of methyl, ethyl, propyl, hydroxy substituted ethyl or propyl and mixtures thereof, preferably methyl, each $R_3$ is selected from the group consisting of hydrogen and hydroxy groups and each n is a number from 1 to 4, preferably from 2 to 3, more preferably 3, with no more than one hydroxy group in any $(C(R_3)_2)$ moiety. The $R_1$ groups can be branched and/or unsaturated. The $R_2$ groups can also be connected to form ring structures. A surfactant of this type is a $C_{10}$–$C_{14}$ fatty acylamidopropylene(hydroxypropylene)sulfobetaine that is available from the Sherex Company under the trade name "Varion CAS sulfobetaine"®.

Typically, the surfactant or mixtures thereof is present in the composition at a level of from 0.01% to 50% by weight of the total composition, preferably from 0.01% to 30% and more preferably from 0.1% to 10%.

A third essential ingredient of the present invention is an antimicrobial essential oil or an active thereof, or a mixture thereof.

Suitable antimicrobial essential oils to be used herein are those essential oils which exhibit antimicrobial activity. By "actives of essential oils" it is meant herein any ingredient of essential oils that exhibit antimicrobial activity. It is speculated that said antimicrobial essential oils and actives thereof act as proteins denaturing agents. Also, said antimicrobial oils and actives thereof are compounds which contribute to the safety profile of a composition comprising them when it is used to disinfect any surface. A further advantage of said antimicrobial oils and actives thereof is that they impart pleasant odor to a composition comprising them without the need of adding a perfume. Indeed combining said antimicrobial essential oil or an active thereof with a surfactant and a chelant, in a composition, allows to deliver not only excellent disinfecting properties on surfaces to be treated with said composition but also good scent while being safe to the surfaces.

Such essential oils include, but are not limited to, those obtained from thyme, lemongrass, citrus, lemons, oranges, anise, clove, aniseed, pine, cinnamon, geranium, roses, mint, lavender, citronella, eucalyptus, peppermint, camphor, sandalwood, rosmarin, vervain, fleagrass, lemongrass, ratanhiae, cedar and mixtures thereof. Preferred antimicrobial essential oils to be used herein are thyme oil, clove oil, cinnamon oil, geranium oil, eucalyptus oil, peppermint oil, mint oil or mixtures thereof.

Actives of essential oils to be used herein include, but are not limited to, thymol (present for example in thyme), eugenol (present for example in cinnamon and clove), menthol (present for example in mint), geraniol (present for example in geranium and rose), verbenone (present for example in vervain), eucalyptol and pinocarvone (present in eucalyptus), cedrol (present for example in cedar), anethol (present for example in anise), carvacrol, hinokitiol, berberine, ferulic acid, cinnamic acid, methyl salycilic acid, methyl salycilate, terpineol and mixtures thereof. Preferred actives of essential oils to be used herein are thymol, eugenol, verbenone, eucalyptol, terpineol, cinnamic acid, methyl salycilic acid and/or geraniol.

Thymol may be commercially available for example from Aldrich, eugenol may be commercially available for example from Sigma, Systems—Bioindustries (SBI)—Manheimer Inc.

Typically, the antimicrobial essential oil or actives thereof or mixture thereof is present in the composition at a level of at least 0.003% by weight of the total composition, preferably from 0.006% to 10%, more preferably from 0.1% to 4% and most preferably of from 0.03% to 2%.

It has now been found that by combining a surfactant, a chelating agent and an antimicrobial essential oil or active thereof, in a composition, that improved disinfecting properties are delivered, even when used under highly diluted conditions. By "improved disinfecting properties" it is meant herein that the disinfection delivered by combining a surfactant, a chelating agent and an antimicrobial essential oil and/or an active thereof, in a composition, is improved as compared to the disinfection delivered by using only one or two of said ingredients, in said composition.

Excellent disinfection is obtained by combining a surfactant, a chelating agent and an antimicrobial essential oil or active thereof according to the present invention on a variety of microorganisms including Gram positive bacteria like *Staphylococcus aureus*, and Gram negative bacteria like *Pseudomonas aeroginosa* as well as on fungi like *Candida albicans* present on surfaces, even if used in highly diluted conditions.

Disinfection properties of a composition may be measured by the bactericidal activity of said composition. A test method suitable to evaluate the bactericidal activity of a composition is described in European Standard, prEN 1040, CEN/TC216 N 78, dated November 1995 issued by the European committee for standardisation, Brussels. European Standard, prEN 1040, CEN/TC216 N 78, specifies a test method and requirements for the minimum bactericidal activity of a disinfecting composition. The test is passed if the bacterical colonies forming units (cfu) are reduced from a $10^7$ cfu (initial level) to a $10^2$ cfu (final level after contact with the disinfecting product), i.e. a $10^5$ reduction of the viability is necessary. A composition comprising a surfactant, a chelating agent and an antimicrobial essential oil or an active thereof passes this test, even if used in highly diluted conditions.

The combination of ingredients according to the present invention may be formulated in a composition being either in a solid, pasty or liquid form. In the case where the compositions according to the present invention are formulated as solids, they will be mixed with an appropriate solvent, typically water, before use. In liquid form, the compositions are preferably but not necessarily formulated as aqueous compositions. Liquid compositions are preferred herein for convenience of use.

In the embodiment, where the compositions according to the present invention are aqueous liquid cleaning compositions, they preferably have a pH as is of not more than 12.0, more preferably from 1 to 10, and most preferably from 2 to 9. The pH of the compositions can be adjusted by using organic or inorganic acids, or alkalinising agents.

As effective disinfection is provided with the combination of ingredients of the present invention the compositions comprising said combination do not require the addition of other antimicrobial compounds. However, if desired in one embodiment of the present invention said compositions may further comprise, as optional ingredients, other antimicrobial compounds like a peroxygen bleach, or mixtures thereof. Preferred peroxygen bleach is hydrogen peroxide, or a water soluble source thereof, or mixtures thereof.

It is believed that the presence of peroxygen bleach especially hydrogen peroxide, persulfate and the like, further contributes to the disinfecting properties of the compositions according to the present invention. Indeed, peroxygen bleach may attack the vital function of the micro-organism cells, for example it may inhibit the assembling of ribosomes units within the cytoplasm of the micro-organism cells. Also peroxygen bleach like hydrogen peroxide, is a strong oxidizer that generates hydroxyl free radicals which attack proteins and nucleic acids. Furthermore, the presence of peroxygen bleach, especially hydrogen peroxide, provides strong stain removal benefits which are particularly noticeable for example in laundry and hard surfaces applications.

As used herein a hydrogen peroxide source refers to any compound which produces hydrogen peroxide when said compound is in contact with water. Suitable water-soluble sources of hydrogen peroxide for use herein include percarbonates, persilicate, persulphate such as monopersulfate, perborates and peroxyacids such as diperoxydodecandioic acid (DPDA), magnesium perphthalic acid and mixtures thereof.

In addition, other classes of peroxides can be used as an alternative to hydrogen peroxide and sources thereof or in combination with hydrogen peroxide and sources thereof. Suitable classes include dialkylperoxides, diacylperoxides, preformed percarboxylic acids, organic and inorganic peroxides and/or hydroperoxides.

The compositions herein may comprise up to 15% by weight of the total composition of a peroxygen bleach or a mixture thereof, preferably from 0.5% to 10%, and more preferably from 1% to 8%.

The compositions according to the present invention may comprise other antimicrobial ingredients that further contribute to the antimicrobial activity of the compositions according to the present invention. Such antimicrobial ingredients include parabens like ethyl paraben, propyl paraben, methyl paraben, glutaraldehyde or mixtures thereof.

The compositions herein may further comprise a variety of other optional ingredients such as solvents, builders, stabilisers, bleach activators, soil suspenders, dye transfer agents, brighteners, perfumes, anti dusting agents, enzymes, dispersant, dye transfer inhibitors, pigments, perfumes, radical scavengers and dyes.

The compositions herein may be packaged in a variety of suitable detergent packaging known to those skilled in the art. The liquid compositions herein may desirably be packaged in manually operated spray dispensing containers, which are usually made of synthetic organic polymeric plastic materials. Indeed, said spray-type dispensers allow to uniformly apply to a relatively large area of a surface to be disinfected the liquid disinfecting compositions suitable to be used according to the present invention, thereby contributing to disinfection properties of said compositions. Such spray-type dispensers are particularly suitable to disinfect vertical surfaces.

Suitable spray-type dispensers to be used according to the present invention include manually operated foam trigger-type dispensers sold for example by Specialty Packaging Products, Inc. or Continental Sprayers, Inc. These types of dispensers are disclosed, for instance, in U.S. Pat. No. 4,701,311 to Dunnining et al. and U.S. Pat. No. 646,973 and U.S. Pat. No. 4,538,745 both to Focarracci. Particularly preferred to be used herein are spray-type dispensers such as T 8500® commercially available from Continental Spray International or T 8100® commercially available from Canyon, Northern Ireland. In such a dispenser the liquid composition is divided in fine liquid droplets resulting in a spray that is directed onto the surface to be treated. Indeed, in such a spray-type dispenser the composition contained in the body of said dispenser is directed through the spray-type dispenser head via energy communicated to a pumping mechanism by the user as said user activates said pumping mechanism. More particularly, in said spray-type dispenser head the composition is forced against an obstacle, e.g. a grid or a cone or the like, thereby providing shocks to help atomise the liquid composition, i.e. to help the formation of liquid droplets.

The compositions of the present invention may also be executed in the form of wipes. By "wipes" it is meant herein disposable towels, e.g., paper towels where a composition according to the present invention is incorporated. In a preferred execution said wipes incorporate a liquid composition. Preferably said wipes are packaged in a plastic box. The advantage of this execution is a faster usage of a disinfecting composition by the user, this even outside the house, i.e. there is no need to pour the liquid compositions according to the present invention on the surfaces to be treated/disinfect and to dry it out with a cloth. In other words, wipes allow disinfection of surfaces in one step.

The compositions according to the present invention may be applied onto any surfaces for disinfection purpose. By "surface" it is meant herein any surface including hard-surfaces like bathroom, kitchen, table tops, refrigerators, and the like as well as fabrics, clothes, carpets and the like. Said compositions according to the present invention may be applied to the surface to be disinfected in its neat form or in its diluted form.

By "diluted form" it is meant herein that the compositions to be used being either in a liquid or solid form may be diluted by the user typically up to 100 times their weight of water, preferably into 80 to 30 times their weight of water, and more preferably 60 to 40 times.

The present invention will be further illustrated by the following examples.

EXAMPLES

The following compositions were made by mixing the listed ingredients in the listed proportions (weight % unless otherwise specified).

| Compositions % by weight | I | II | III | IV | V | VI |
|---|---|---|---|---|---|---|
| Hydrogen peroxide | 7.0 | — | — | 2 | 4 | — |
| Thyme oil | — | 0.4 | — | — | 0.5 | — |
| Clove oil | 0.5 | — | — | 0.2 | — | 0.1 |
| Geranium oil | — | 0.2 | — | — | — | — |
| Eucalyptus oil | 0.2 | — | 0.2 | 0.2 | — | 0.2 |
| geraniol | — | — | 0.5 | — | 0.5 | 0.1 |
| Alkyl sulphate | 4 | 3 | 10 | 1 | 4 | 0.5 |
| DETPMP | 0.1 | 0.15 | 0.15 | 0.1 | 0.15 | 0.2 |
| Water and minors H2SO4 up to pH 4 | | | up to 100% | | | |

| Compositions % by weight | VII | VIII | IX | X | XI | XII |
|---|---|---|---|---|---|---|
| Hydrogen peroxide | 7.0 | — | — | 2 | 4 | — |
| Thyme oil | — | 0.4 | — | — | 0.5 | — |
| Clove oil | 0.5 | — | — | 0.2 | — | 0.1 |
| Geranium oil | — | 0.2 | — | — | — | — |
| Eucalyptus oil | 0.2 | — | 0.2 | 0.2 | — | 0.2 |
| geraniol | — | — | 0.5 | — | 0.5 | 0.1 |
| Betaine | 1.5 | 0.05 | — | 0.05 | — | 0.05 |
| Amine oxide | 3 | 0.9 | — | 1 | — | 0.9 |
| Alkyl sulphate | — | — | 1.5 | — | 4 | — |
| DTPA | 0.1 | — | 0.15 | 0.1 | 0.15 | — |
| DETPMP | — | 0.15 | — | — | — | 0.2 |
| Water and minors H2SO4 up to pH 4 | | | up to 100% | | | |

DETPMP is diethylene triamine penta methylene phosphonate
DTPA is diethylene triamine pentacetate
Alkyl sulfate is a C10 alkyl sulphate
Betaine is coco alkyldimethyl betaine available from Albright & Witson under the trade name of Empigen BB/L ®.
Amine oxide is N-decyldimethyl amine oxide The compositions of the examples above are according to the present invention, they may be used neat or diluted, e.g., composition I and VII may be used at a dilution level of 1:50 and composition III at a dilution level of 1:25, to provide effective disinfecting performance on the surface treated. Indeed, these compositions pass the prEN 1040 test of the European committee of standardisation.

What is claimed is:

1. A disinfecting composition comprising:
   (a) from about 0.001% to about 5% by weight of a chelating agent;
   (b) from about 0.01% to about 50% by weight of a surfactant of the formula:

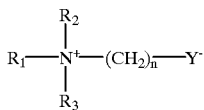

wherein R1 is an alkyl radical containing from 1 to 24 carbon atoms; R2 and R3 are independently an alkyl radical containing from 1 to 3 carbon atoms; n is an integer from 1 to 10; Y is selected from the group consisting of carboxyl and sulfonyl radicals; and wherein the sum of R1, R2 and R3 radicals is from 14 to 24 carbon atoms;
   (c) from about 0.003% to about 10% by weight of an antimicrobial essential oil; and
   (d) from about 0.5% to about 15% by weight of a peroxygen bleach.

2. A disinfecting composition according to claim 1 wherein said antimicrobial essential oil is selected from the group consisting of thyme oil, lemongrass oil, citrus oil, lemon oil, orange oil, anise oil, clove oil, aniseed oil, cinnamon oil, geranium oil, rose oil, lavender oil, citronella oil, eucalyptus oil, peppermint oil, mint oil, camphor oil, sandalwood oil, cedar oil, rosmarin oil, pine oil, vervain oil, fleagrass oil, ratanhiae oil, and mixtures thereof.

3. A disinfecting composition according to claim 1 wherein said chelating agent is selected from the group consisting of phosphonate chelating agents, amino carboxylate chelating agents, carboxylate chelating agents, polyfunctionally-substituted aromatic chelating agents and mixtures thereof.

4. A disinfecting composition according to claim 3 wherein said chelating agent is selected from the group consisting of etidronic acid, an alkali metal salt of ethane 1-hydroxy diphosphonate, nitrilo trimethylene phosphonate, ethylene diamine tetra methylene phosphonate, diethylene triamine penta methylene phosphonate, dihydroxydisulfobenzene, ethylenediamine N,N'-disuccinic acid, ethylene diamine tetra acetate, ethylene diamine penta acetate, N-hydroxyethylenediaminetriacetate, nitrilotriacetate, ethylenediamine tetrapropionate, triethylenetetraaminehexa-acetate, ethanoldiglycine, propylene diamine tetracetic acid, methyl glycine di-acetic acid, malonic acid, salicyic acid, glycine, aspartic acid, glutamic acid, dipicolonic acid, and mixtures thereof.

5. A disinfecting composition according to claim 1 wherein said peroxygen bleach is selected from the group consisting of hydrogen peroxide, source of hydrogen peroxide, dialkylperoxide, diacylperoxides, and mixtures thereof.

6. A disinfecting composition according to claim 5 wherein said source of hydrogen peroxide is selected from the group consisting of perborates, percarbonates, persulfates, monopersulfates, peroxyacids, magnesium perpthalic acid and mixtures thereof.

7. A disinfecting composition according to claim 1 wherein R1 is an alkyl radical containing from 8 to 18 carbon atoms and n is an integer from 1 to 6.

8. A disinfecting composition according to claim 1 wherein said composition further comprises:
   (e) an optional ingredient selected from the group consisting of dye transfer agents, anti-dusting agents, radical scavengers and mixtures thereof.

9. A disinfecting composition according to claim 2 wherein said antimicrobial essential oil is selected from the group consisting of orange oil, cinnamon oil, rose oil, lavender oil, peppermint oil, mint oil, camphor oil, sandalwood oil, cedar oil, rosmarin oil, vervain oil, fleagrass oil, ratanhiae oil, and mixtures thereof.

10. A disinfecting composition according to claim 1 wherein composition further comprises:
    (f) another antimicrobial ingredient selected from the group consisting of glutaraldehyde, ethyl paraben, propyl paraben, methyl paraben and mixtures thereof.

11. A disinfecting composition according to claim 1 wherein said disinfecting composition is an aqueous composition with a pH of less than 12.0.

12. A method of using the disinfecting composition according to claim 1, comprising the step of diluting the disinfecting composition with water.

13. A method of using the disinfecting composition according to claim 1, comprising the step of applying said disinfecting composition directly to a sponge or a washcloth.

14. A method of disinfecting a surface comprising applying the disinfecting composition according to claim 1, to a surface in need of disinfection.

15. A method of disinfecting a surface according to claim 14 wherein said disinfecting composition is applied neat or in diluted form.

* * * * *